United States Patent [19]
Waldie et al.

[11] Patent Number: 4,649,738
[45] Date of Patent: Mar. 17, 1987

[54] FLUIDIC PERMEABILITY MEASUREMENT BRIDGE

[75] Inventors: Arthur H. Waldie, Organ; Marvis N. Gillum; James M. Wilkes, both of Las Cruces, all of Minn.

[73] Assignee: The United States of America as represented by the Secretary of Agriculture, Washington, D.C.

[21] Appl. No.: 818,564

[22] Filed: Jan. 13, 1986

[51] Int. Cl.$^4$ ............................................. G01N 15/08
[52] U.S. Cl. ...................................... 73/38; 73/32 R; 73/37.6
[58] Field of Search ............... 73/38, 37.7, 37.6, 32 R

[56] References Cited

U.S. PATENT DOCUMENTS 3,218,844 11/1965 Kleist et al. ................... 73/37.6 X
4,311,037 1/1982 Gotchel et al. ........................ 73/38
4,471,649 9/1984 Cronshaw ............................ 73/38
4,495,796 1/1985 Hester et al. ......................... 73/38
4,506,542 3/1985 Rose ....................................... 73/38

FOREIGN PATENT DOCUMENTS 980058 1/1965 United Kingdom ................. 73/38

OTHER PUBLICATIONS

A. H. Waldie et al., "Automatic Moisture Sensor for Measurement and Control of Cotton Ginning Processes", J. Eng. Indus. 105: 27-30 (Feb. 1983).

Primary Examiner—Michael J. Tokar
Assistant Examiner—Joseph W. Roskos
Attorney, Agent, or Firm—M. Howard Silverstein; David G. McConnell; Curtis P. Ribando

[57] ABSTRACT

Physical properties relating to permeability and porosity of a material in a conveying fluid medium are determined in a device designed to measure the pressure differential between a first stream of fluid applied directly to the material in the medium and a second stream applied to a referencing plenun containing only the medium. The system is sensitive to the component of flow resistant imparted by the material itself without measuring the pressure drop across the entire thickness of material. The invention finds particular application in determining the permeability of cotton at various stages of the ginning operation for the ultimate purpose of monitoring and controlling the moisture content.

20 Claims, 4 Drawing Figures

FLUIDIC PERMEABILITY MEASUREMENT BRIDGE

BACKGROUND OF THE INVENTION

1. Field of the Invention

A measure of the fluidic permeability of a porous material is often necessary for product evaluation. It can often be used to determine other characteristics of the material. For example, in a cotton fiber batt, the bulk density of the material can be related to the material's permeability to fluid flow. The density measurement can then be used in conjunction with other measurements for determining properties such as micronaire and moisture content.

Cotton fiber moisture content is one of the most significant parameters needed for process control and performance optimization of commercial cotton gins. The moisture level affects the fiber length, fiber length uniformity, and the removal of trash from the cotton lint. It is necessary to correlate moisture readings with permeability measurements of both the seed cotton and the cotton lint in order to obtain an accurate measure of moisture content.

2. Description of the Prior Art

Most conventional systems for measuring permeability of a material require totally confining a static volume of the material in a chamber during the measurement, thereby fixing its dimensional shape. A fluid is then passed through the material and the flow and pressure drop across the material are measured and used to determine the permeability. This method is not well suited for making high-speed permeability measurements in an industrial process in that it involves a continuous side-stream sampling of the feed stream. Such a system is shown for example by Rose in U.S. Pat. No. 4,506,542. The sample chamber therein comprises four fluid impervious sides, and front and back porous barriers. The pressure and flow rate of the fluid is regulated and measured on either side of the porous test material.

Various devices for measuring the permeability of the moving porous web have arisen from the cigarette paper manufacturing industry. For example, in U.S. Pat. No. 4,311,037, Gotchel et al. passes a paper web over a sensing head having one or more apertures through which a vacuum is drawn on the web. A differential pressure transducer compares the static pressure within the aperture to a reference pressure. The output of the transducer is used to generate a continuous reading of the pressure drop across the web representative of the permeability. In U.S. Pat. No. 4,471,649, Cranshaw shows holding one side of a moving sheet over the inlet of a first gas-flow chamber by directing a gaseous medium from the outlet of a second flow chamber against the opposite side of the sheet. The permeability of the sheet to the gaseous medium is measured by a pressure transducer connected across a low-impedance, multicapillary laminar-flow device. Hester et al. in U.S. Pat. No. 4,495,796 discloses a device for monitoring both the pressure drop and the flow rate of a fluid passing through a sensing head in contact with a moving web. The volumetric flow rate is determined by directing the fluid through a laminar-flow element, sensing the pressure differential across the element by means of a first transducer, and generating a signal analogous to the flow rate. A signal representing the pressure drop across the web as measured by a second transducer is used in conjunction with the flow rate signal to develop a signal representing permeability.

It is apparent from the above patents that the art-established method for determining permeability requires measuring the pressure drop across the entire thickness of the material. Moreover, in no case does the prior art dealing with permeability measurement of a moving material address the effect on the measurement of the fluid medium in the pores or interstices of the material. In the case of paper webs such as disclosed in Gotchel et al., Cranshaw, and Hester et al., the effect of the medium in the pathways between the fibers would obviously be minor in comparison to that in a cotton batt. It can be appreciated that in materials of relatively low bulk density, the density of fluid medium could have a substantial influence on the apparent permeability of the material. In such cases, the effects of the temperature, pressure, and humidity on the density of the medium become significant.

SUMMARY OF THE INVENTION

The measurment bridge system of this invention is designed for use in determining a physical property of a solid material having permeability to an applied fluid wherein the material is in a conveying fluid medium and the physical property is a function of the material's resistance to the flow of the applied fluid. The bridge system is designed so as to null the effect of the conveying medium on the measurement, which will thereby be independent of changing physical properties of the medium. The device comprises:
  a. a test head having a surface for contact by the material;
  b. at least one measurement orifice in the surface;
  c. at least one reference plenum in communication with the conveying fluid medium;
  d. at least one reference orifice opening into the reference plenum;
  e. an applied fluid supply;
  f. means for dividing the applied fluid supply into a measurement stream in communication with the measurement orifice and a reference stream in communication with the reference orifice;
  g. a means for measuring the pressure differential between the measurement stream and the reference stream.

The method of the invention for determining a physical property of a solid material having permeability to an applied fluid in a conveying fluid medium comprises:
  a. feeding the material into contact with a test head surface;
  b. supplying a first applied fluid stream under pressure to at least one measurement orifice in the surface, whereby the applied fluid is induced to flow directly into the material;
  c. supplying a second applied fluid stream under pressure to at least one reference orifice opening into a reference plenum in communication with the conveying fluid medium, whereby the applied fluid passes through the plenum prior to entering the material;
  d. determining the pressure diffential between the first fluid stream and the second fluid stream; and
  e. calculating the physical property of the material from the pressure differential.

In accordance with this discovery, it is an object of the present invention to provide an apparatus and method for use in determining a property of a solid material related to fluid flow through the material when it is not possible or practical to confine the material in three dimensions.

More particularly, it is an object of the invention to provide an apparatus and method for use in accurately determining a physical property as a function of resistance to fluid flow of a continuously moving mass of solid material in a nonstable conveying fluid medium; that is, one in which the density of the medium is susceptible to fluctuation as the result of changes in temperture, pressure, or humidity.

A further object of the invention is to measure the resistance to fluid flow of a continuously moving mass of solid material in a fluid medium without the need to measure the pressure drop of the applied fluid throughout the entire thickness of the material.

Another object of the invention is to provide an apparatus and method for generating information useful in determining properties such as permeability, bulk density, and moisture content of cotton at various stages of the cotton ginning process to enable industrial control and automation of the operation.

Other objects and advantages of this invention will become readily apparent from the ensuing description.

DETAILED DESCRIPTION OF THE INVENTION

Figure 1:
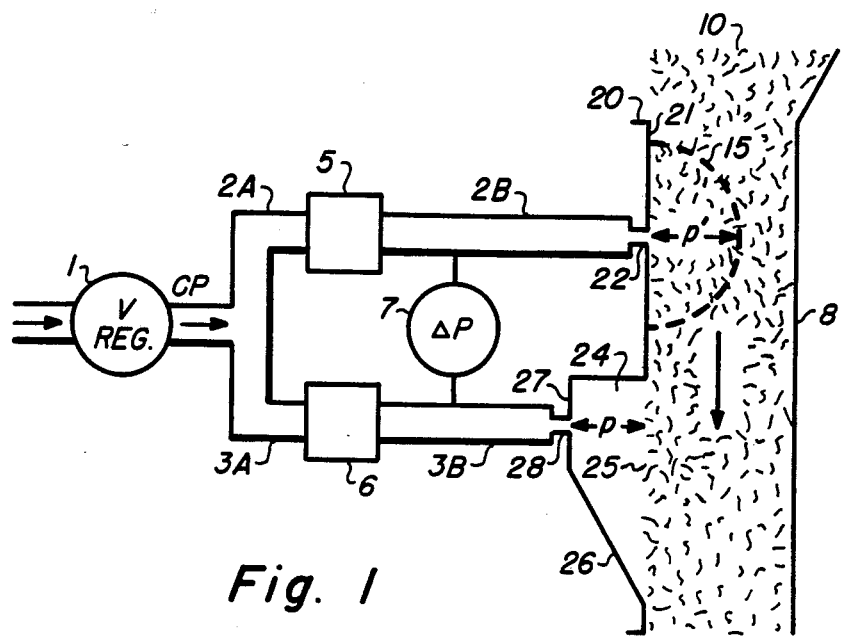
FIG. 1 is a simplified schematic drawing depicting the essential features of the invention in relation to the test material.

The formal definition of permeability K of a porous, solid material is the volume of an applied fluid of unit viscosity passing through a unit cross section of the material in unit time under the action of a unit pressure gradient. Permeability is strictly a function of the structure of the material in question, and is entirely independent of the nature of the applied fluid. Permeability can be related to porosity by the general formula:

$$K = f(\phi, k) \qquad (1)$$

where $\phi$ is the porosity of the material during the measurement, and $k$ is a factor which is related to the path which the fluid must take to get through the material. The factor $k$ is a function of the material's shape, orientation, and packing geometry over the density range of the measurement, and it is usually determined by experimentation. Porosity is, by definition, the volume fraction of pore space in the material, which can be expressed as:

$$\phi = 1 - D_b/D \qquad (2)$$

where $D_b$ is the material's bulk density, and $D$ is the material's true density. This equation shows that the porosity decreases as the bulk density increases. When the bulk density is equal to the true density, then porosity equals zero. If a material is permeable, then the pore space forms continuous pathways through the material, therefore allowing fluid flow. Assuming the material is permeable, and inert to the fluid passing through it, then an equation can be written relating the porosity of a given material and its specific physical characteristics to its permeability.

The measurement bridge system described herein correlates the resistance of a material fluid medium to the flow of a fluid applied to the material along a single interface of the material and measurement surface. The material may be any porous substance, such as fibers, granules, or particles, which is permeable to an applied fluid, and which is not uncontrollably displaced by the applied fluid. Illustrative materials without limitation thereto include seed cotton, cotton lint, wool, cloth, paper, hay, and soil.

The term "conveying fluid medium" as used herein is intended to refer to the gas or liquid which surrounds the test material under the conditions of measurement. It is of course understood that only that portion of the conveying fluid which is present in any of the continuous pathways of the test material through which the measurement is taken is of concern. Fluid within discontinuous or "dead end" pores of the material will not have a significant effect on the apparent permeability. For instance, in the case of a cotton batt, the interstitial fluid of concern is that which is between the individual cotton fibers. For purposes of the invention, the conveying fluid need not be a moving stream in the sense that it is transporting the material, but may in fact be the fluid which simply surrounds a static batch of test material. In a typical, pneumatic transport, cotton ginning operation, the conveying fluid will be ambient air which is drawn into the cotton stream and tempered by the moisture present in the cotton.

The applied fluid may be any compressible fluid, preferably a gas such as air, which is clean and not reactive with the system components or the test material. Referring to FIG. 1, the applied fluid from a supply 1 at a regulated pressure is split into two streams, measurement stream 2A, and reference stream 3A. Streams 2A and 3A are regulated to a constant flow by mass-flow regulators 5 and 6, respectively, which may simply comprise regulating orifices of a predetermined diameter as known in the art. It is desireable to match the regulators so that the fluid flowing through them is as nearly equal in mass as possible.

Downstream from regulator 5, the flow-regulated measurement stream 2B is directed to one or more fluidic restrictors, hereafter referred to as measurement orifices 22 opening into the face 21 of sensing head 20. The facial surface should be sufficiently smooth so as to allow unimpeded movement of the test material forced against it.

Figure 4:
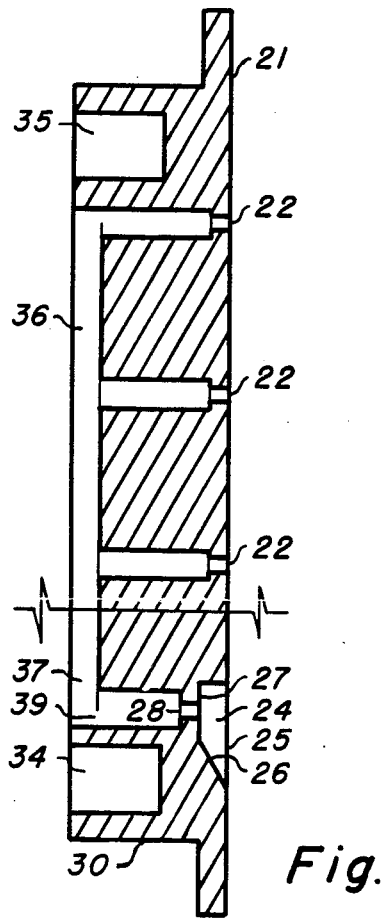
FIG. 4 is a cross-sectional view of the test head taken along the line 4—4 of FIG. 3.

In communication with the conveying fluid medium, and preferably recessed in the surface of face 21, is at least one reference plenum 24. It is designed to allow the test material 10 to pass over its mouth 25 without accumulating inside the plenum. For this reason, it is advantageous to bevel the downstream wall 26 of the plenum in the direction of material flow as shown in FIGS. 1 and 4. Opening into the back wall 27 of the plenum are one or more fluidic restrictors, hereafter referred to as reference orifices 28. The reference orifices are dimensioned to restrict the flow of regulated reference stream 3B in the same manner and to the same extent as measurement orifices 22 restrict measurement stream 2B. Thus, both the measurement and reference legs of the bridge system are nearly identically configured with the exception of the effective interface beween the fluid exhausting from the respective orifices and the test material. Compensation for minor discrepancies in fluid flow between the respective legs can be made in the electronics associated with the pressure measurement.

The measurement orifice system exhausts directly into a zone of the test material, thereby allowing the material to impart a component of back pressure or resistance to the applied fluid through the orifice while the applied fluid has a large amount of kinetic energy. The other major component of flow resistance imparted to the applied fluid is the result of the conveying fluid medium. As previously discussed, in an environment having changing conveying fluid conditions, this latter component of resistance is variable. For purposes of compensating for, or nulling out, the effect of this variable component, the reference orifice system exhausts directly into the conveying fluid in plenum 24. This allows for dissipation of most of the applied fluid's kinetic energy prior to passing into the test material. The area of test material at the mouth of the plenum to which the applied fluid exhausting from the reference orifice is initially exposed is considerably greater than that exposed to the fluid exhausting from the measurement orifice. The result is that at the plenum mouth 25, the component of resistance to the applied fluid flow attributed to the test material is relatively insignificant in comparison to the component of resistance attributed to the conveying fluid. Therefore the back pressure imparted to stream 3B from outside the reference orifice is due primarily to the conveying fluid component of resistance. Consequently, the pressure differential $\Delta P$ between streams 2B and 3B as measured by pressure transducer 7 or the like essentially represents the test material component of resistance.

The pressure of the applied fluid exiting the measurement and reference orifices should be preselected so that the test material is not significantly displaced from the face 21. To promote compliance of the material to the facial surface, it can be restrained by providing a baffle 8 opposite the sensing head. In a cotton ginning operation, sensors are advantageously positioned in the receiving hoppers or flow control units feeding the gin saw stand and lint cleaner. The depth of the cotton stored at these points is sufficient to give a material density that is uniform and high enough to provide good surface contact between the cotton and the face of the sensor. In this environment, the back and side walls of the receiving hopper or flow control unit are the functional equivalent of the baffle 8.

The principle of the measurement system described above relies upon a measurement volume which is determined by the characteristics of the reference plenum system. For a measurement orifice 22, points surrounding the orifice at a given pressure define an equipressure surface 15. We define an effective measurement volume as the volume enclosed by an equipressure surface surrounding the measurement orifice, which is at a pressure equal to the pressure of the applied fluid at the mouth 25 of the reference plenum where the applied fluid interfaces with the test material. Thus, by definition, the pressure drop p across the reference plenum is the same as the pressure drop p' across the effective volume. As discussed above, the pressure drop p is primarily a function of the backpressure imparted by the conveying fluid, whereas p' is a function of the backpressure from both the conveying fluid and the test material. By making the mouth of the reference plenum, and thus the effective volume sufficiently large, the pressure at the equipressure surface approaches that of the conveying fluid. The component of backpressure attributed to the test material within the effective volume then approaches the theoretical maximum component of backpressure which the entire thickness of material will impart to the applied fluid at a given pressure of stream 2B. Of course the larger the effective volume, the more closely the observed p' approaches the theoretical maximum, and the more accurate the measurement. However, as the effective volume increases, each incremental increase in p' varies as an inverse power of the distance from the orifice, and rapidly becomes insignificant. A practical limitation on the size of the reference plenum mouth 25 is imposed by the flow characteristics of the test material. The mouth dimensions should not exceed those which would allow significant encroachment of the material into the plenum, thereby reducing the effective volume.

The less permeable the material is to the applied fluid, the higher the pressure throughout the measurement orifice and throughout stream 2B, and the greater the value of $\Delta P$. A relation between the permeability value and $\Delta P$ can be determined either empirically, or by theoretical considerations involving Darcy's law, Bernoulli's principle, and idealized models of the system geometry.

In systems where the test material and conveying fluid medium are at other than atmospheric pressure, the pressure transducer benefits from a high signal-to-noise ratio as compared to prior art systems which are designed to reference the atmosphere.

Figure 2:
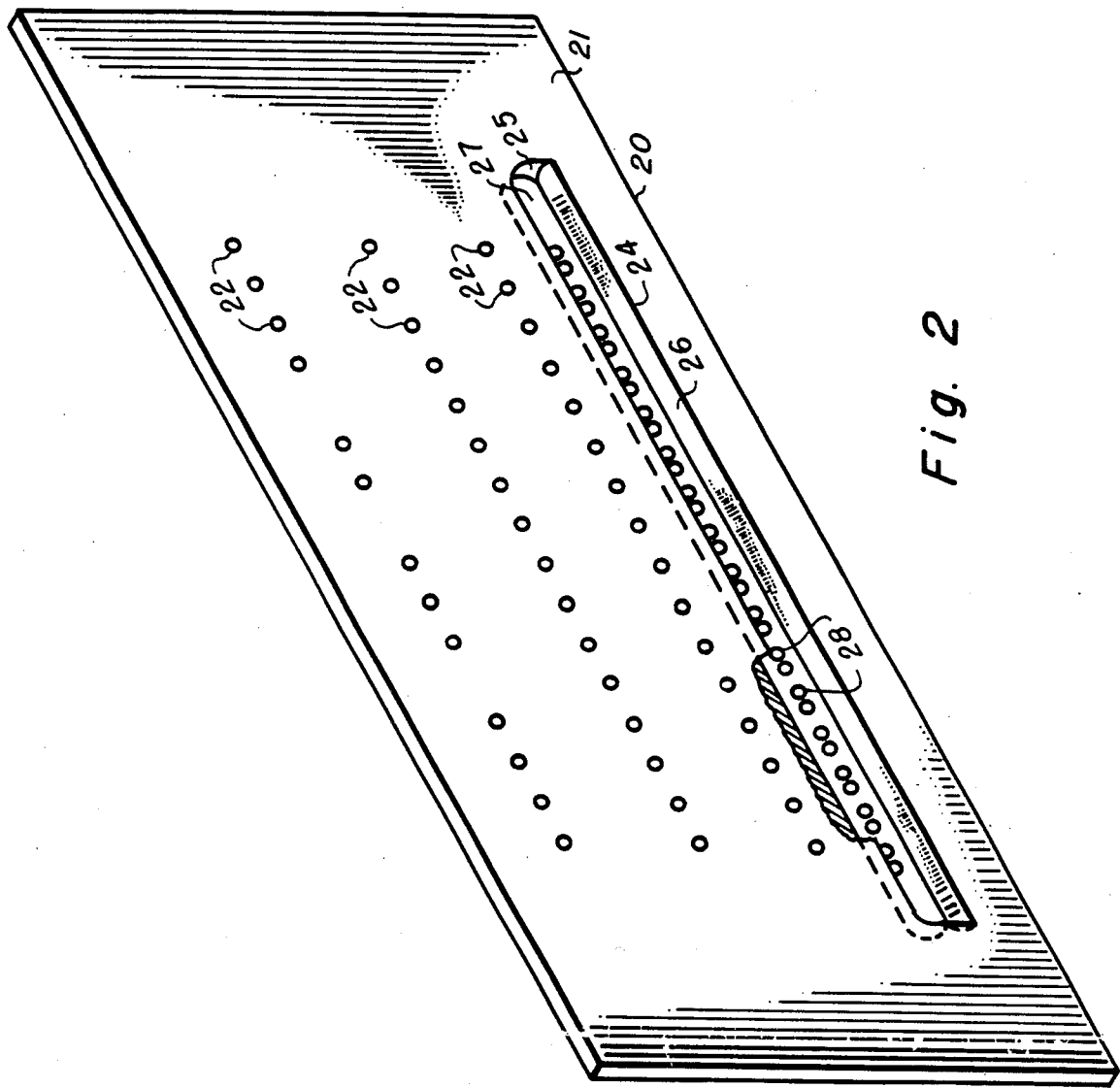
FIG. 2 is a front perspective view of a preferred embodiment of the sensing head.
Figure 3:
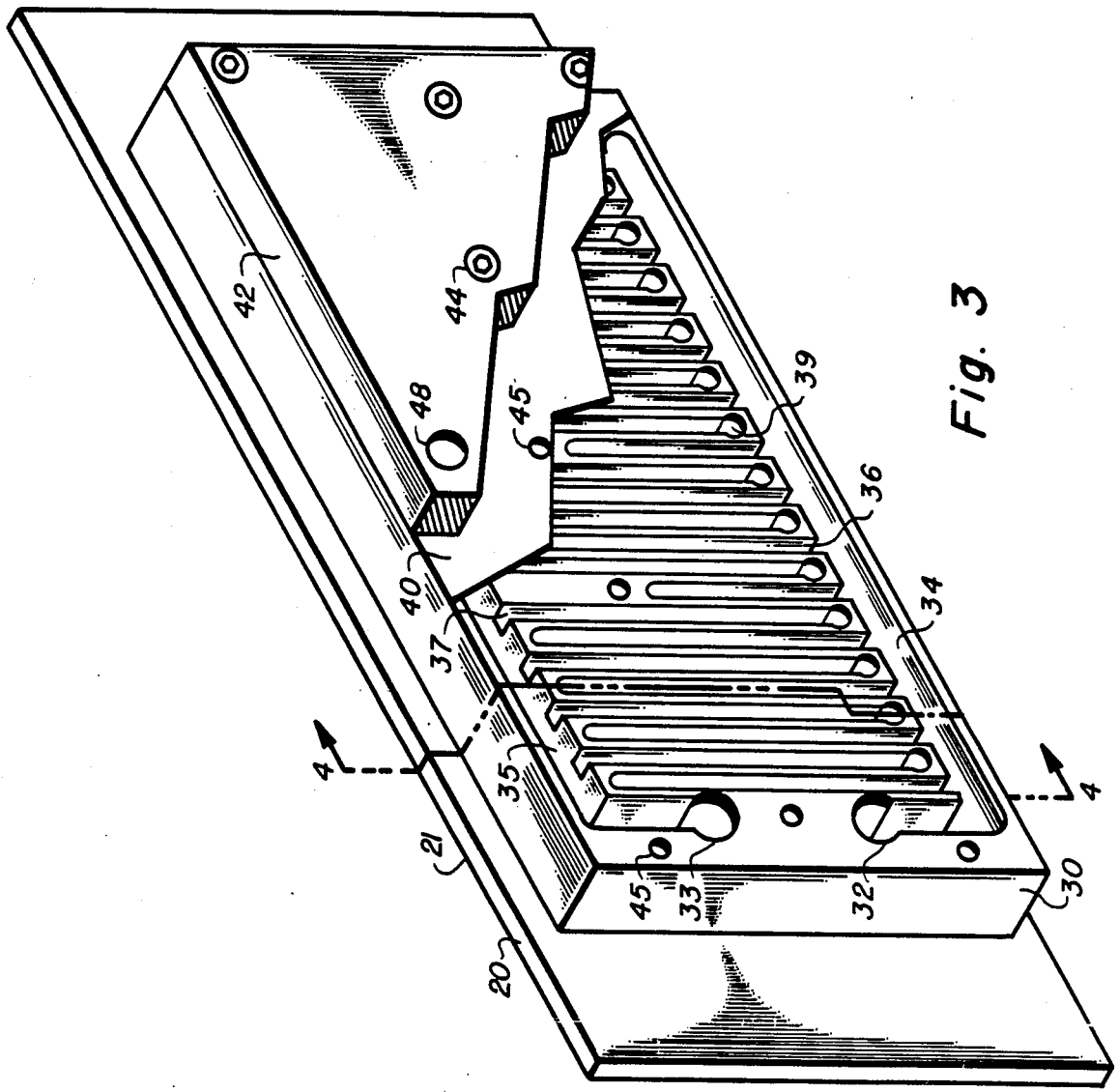
FIG. 3 is a rear perspective view of the sensing head depicted in FIG. 2.

FIGS. 2-4 show the sensing head 20 in an embodiment of the invention reduced to practice for use in measuring the permeability of seed cotton and cotton lint. While we have demonstrated that the device can be machined from metal, it could also be produced from molded plastic or the like.

The face 21 comprises a flat, smooth plate as best illustrated in FIG. 2. Spaced across the surface of the plate are a plurality of tubular measurement orifices 22. Neither the specific pattern nor spacing of the orifices is especially critical, but both are dictated in part by the design of the fluid stream distribution manifold described below. The number of holes is of course a factor in the precision of the measurement, in that it allows for averaging the pressure drop p' over a plurality of effective measurement volumes throughout the test material. The reference plenum 24 is positioned in the face plate so that tubular reference orifices 28 in back wall 27 are contained within approximately the same width of field or exposure as the measurement orifices with respect to the direction of material flow. With this arrangement, the same sample of material is subjected to both streams of applied fluid, thereby further enhancing reliability of the measurement. The mouth 25 of reference plenum 24 is flush with the surface of face 21. Downstream plenum wall 26 is sloped so that the mouth 25 of the plenum is wider than the back to facilitate material flow past the mouth.

A rear view of the sensing head 20 is shown in FIG. 3. Affixed to the back of face plate 21 is fluid stream distribution manifold 30. After passage through a screen-type diffuser (not shown), the regulated measurement stream 2B enters the manifold at inlet 32 and is distrsibuted by header 34 to the several channels 36 which communicate with the measurement orifices 22 as best illustrated in FIG. 4. Similarly, in the reference leg of the device, the diffused reference stream 3B enters the manifold at inlet 33 and is distributed by header 35 to the several channels 37 which communicate with the reference orifices located within the terminus 39 of each channel. When the manifold is constructed from a thermal conductor, the staggered relationship between channels 36 in the measurement leg and channels 37 in the reference leg permits heat exchange between the respective streams. Minor temperature diffentials which may arise between the two streams will thereby be dissipated prior to discharge from the face plate. The fluid passages of the measurement leg in the manifold are sealed from those of the reference leg by virtue of gasket 40 which is compressed between manifold 30 and backing plate 42. Plate 42 is secured to the manifold by any conventional means such as cap screws 44 and tapped holes 45.

A port 48 is provided in backing plate 42 and gasket 40 to enable the reference side of the pressure transducer 7 or its equivalent to communicate with reference stream 2B in header 35. A counterpart port (not shown) is also provided for the measurement side of the transducer to communicate with the measurement stream in header 34.

It is understood that the foregoing detailed description is given merely by way of illustration and that modification and variations in the specific design and configuration of the described device may be made therein for purposes of a particular application without departing from the spirit and scope of the invention.

We claim:

1. A device for use in determining a physical property of a solid material having permeability to an applied fluid in a conveying fluid medium comprising:
   a. a test head having a surface for contact by the material;
   b. at least one measurement orifice in the surface;
   c. at least one reference plenum in communication with the conveying fluid medium;
   d. at least one reference orifice opening into the reference plenum;
   e. an applied fluid supply;
   f. means for dividing the applied fluid supply into a measurement stream in communication with the measurement orifice and a reference stream in communication with the reference orifice; and
   g. a means for measuring the pressure differential between the measurement stream and the reference stream.

2. A device as described in claim 1 and further comprising:
   h. a constant mass flow regulator in each of the fluid streams.

3. A device as described in claim 2 wherein the constant mass flow regulators are balanced for providing an equal flow rate to each of the fluid streams.

4. A device as described in claim 1 wherein the means for measuring the pressure differential between the measurement stream and the reference stream is a pressure transducer.

5. A device as described in claim 1 wherein the reference plenum is recessed in the test head surface.

6. A method for determining a physical property of a solid material having permeability to an applied fluid in a conveying fluid medium comprising:
   a. feeding the material in the fluid medium into contact a test head surface;
   supplying a first applied fluid stream under pressure to at least one measurement orifice in the surface, whereby the applied fluid is induced to flow directly into the material;
   c. supplying a second applied fluid stream under pressure to at least one reference orifice opening into a reference plenum in communication with the conveying fluid, whereby the applied fluid passes through the plenum prior to entering the material;
   d. determining the pressure differential between the first fluid stream and the second fluid stream; and
   e. calculating the physical property of the material from the pressure differential.

7. The method of claim 6 wherein the material is a fiber.

8. The method of claim 6 wherein the material is a cotton fiber batt.

9. The method of claim 6 wherein the conveying fluid medium is gaseous.

10. The method of claim 6 wherein the applied fluid is gaseous.

11. The method of claim 6 wherein the flow rates of the first applied fluid stream and the second applied fluid stream are equal.

12. The method of claim 6 wherein said physical property is permeability.

13. The method of claim 6 wherein said physical property is bulk density.

14. A method for determining a physical property of a solid material having permeability to an applied fluid in a conveying fluid medium comprising:
   a. dividing a pressurized supply of applied fluid into a first stream and a second stream;
   b. directing the first applied fluid stream under pressure to a first zone wherein depressurization of the stream occurs substantially within a mixture of the material and the conveying fluid medium;
   c. directing the second applied fluid stream under pressure to a second zone wherein depressurization occurs substantially in the conveying fluid medium prior to the stream interfacing the material;
   d. determining the pressure differential between the first fluid stream and the second fluid stream upstream of said first and second zones; and
   e. calculating the physical property of the material from the pressure differential.

15. The method of claim 14 wherein the material is a fiber.

16. The method of claim 14 wherein the material is a cotton fiber batt.

17. The method of claim 14 wherein the conveying fluid medium and the applied fluid are both gaseous.

18. The method of claim 14 wherein the flow rates of the first applied fluid stream and the second applied fluid stream are equal.

19. The method of claim 14 wherein said physical property is permeability.

20. The method of claim 14 wherein said physical property is bulk density.

* * * * *